| (12) | United States Patent | (10) Patent No.: | US 7,692,057 B2 |
|---|---|---|---|
| | Xie et al. | (45) Date of Patent: | Apr. 6, 2010 |

(54) PROCESS FOR PRODUCING LOWER OLEFINS BY USING MULTIPLE REACTION ZONES

(75) Inventors: Zaiku Xie, Shanghai (CN); Juntao Liu, Shanghai (CN); Weimin Yang, Shanghai (CN); Siqing Zhong, Shanghai (CN); Yanhui Yuan, Shanghai (CN); Huiming Zhang, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 239 days.

(21) Appl. No.: 11/502,520

(22) Filed: Aug. 11, 2006

(65) Prior Publication Data

US 2007/0038010 A1   Feb. 15, 2007

(30) Foreign Application Priority Data

Aug. 15, 2005   (CN) .................. 2005 1 0028811
Aug. 15, 2005   (CN) .................. 2005 1 0028812

(51) Int. Cl.
    *C07C 4/02*      (2006.01)
    *C10G 51/04*     (2006.01)
    *C10G 11/05*     (2006.01)
(52) U.S. Cl. .................... 585/653; 585/651; 208/74; 208/75; 208/120.01; 208/122
(58) Field of Classification Search ......... 585/651–653, 585/312, 324; 208/72, 74, 75, 113, 121, 208/122, 120.01
See application file for complete search history.

(56) References Cited

U.S. PATENT DOCUMENTS

2003/0181777 A1 *   9/2003   Powers et al. ............... 585/648
2005/0096492 A1 *   5/2005   Dath et al. .................. 585/653

* cited by examiner

*Primary Examiner*—In Suk Bullock
(74) *Attorney, Agent, or Firm*—Birch, Stewart, Kolasch & Birch, LLP.

(57) ABSTRACT

The present invention provides a process for producing lower olefins by catalytic cracking a feedstock comprising an olefins-enriched mixture containing C4 or higher olefins and optionally an organic oxygenate compound. The technical problem mainly addressed in the present invention is to overcome the defects presented in the prior art including low yield and selectivity of lower olefins as the target products, and short regeneration period of catalyst. The present process, which is carried out under the conditions of catalytic cracking olefins and adopts as a feedstock an olefins-enriched mixture containing one or more C4 or higher olefins and optionally an organic oxygenate compound, comprises the steps of: a) letting the feedstock firstly enter a first reaction zone to contact with a first crystalline aluminosilicate catalyst having a $SiO_2/Al_2O_3$ molar ratio of at least 10, to thereby produce a first reaction effluent containing lower olefins; b) letting the first reaction effluent enter in turn at least one second reaction zone to contact with a second crystalline aluminosilicate catalyst having a $SiO_2/Al_2O_3$ molar ratio of at least 10, to thereby produce a second reaction effluent containing lower olefins; and c) separating lower olefins from the second reaction effluent; wherein the reaction temperatures in the first and second reaction zones are controlled. The present process, which desirably solves the above technical problem, can be used in industrial production of lower olefins.

22 Claims, No Drawings

PROCESS FOR PRODUCING LOWER OLEFINS BY USING MULTIPLE REACTION ZONES

CROSS REFERENCE

The present application claims the priorities of the patent applications with Serial. No. 200510028811.3 and No. 200510028812.8 as filed with the State Intellectual Property Office of China on Aug. 15, 2005, which are incorporated herein for reference in their entirety for all purposes.

TECHNICAL FIELD

The present invention relates to a process for producing lower olefins, and in particular to a process for producing lower olefins by virtue of catalytic cracking of $C_4$ or higher olefins.

BACKGROUND ART

Petrochemical industry is an important supporting industry in national economy, and supplies a large quantity of chemical raw materials for various departments including industry, agriculture, communication and national defense, which is thus one of the industrial sectors taking correlative and leading action in national economy. Lower olefins are one of the most important basic raw materials constituting modern petrochemical industry.

For instance, propylene is mainly used for the production of polypropylene, cumene, oxo alcohol, acrylonitrile, propylene oxide, acrylic acid, isopropanol and etc., wherein polypropylene accounts for more than half of the demand for propylene in the world.

At present, 67% of propylene in the world is derived from by-products in the production of ethylene by steam cracking, 30% of which is derived from by-products in the production of gasoline and diesel oil by catalytic cracking unit (FCC) in refinery, and low amount of which (about 3%) is obtained from dehydrogenation of propane and metathesis reaction of ethylene-butylene. It is predicted that the demand of propylene in the future will be increased in a higher rate than the supply thereof. Considering the relatively higher rate of increase in term of demand of propylene, and the situation of "demand exceeds supply" presented in conventional production modes, it is necessary to recur to other various new techniques of increasing yield of propylene for the purpose of supplementing the demand of propylene.

In recent periods, under the influence of strong demand for polyolefins and alkyl aromatic compounds, the demand of lower olefins tends to be rapidly increased, while the conventional production modes of lower olefins cannot satisfy the rapidly increased demand of the market for lower olefins, thus it is necessary to recur to other various new techniques of increasing yield of lower olefins for the purpose of supplementing the demand of lower olefins.

On the other hand, there are quite a lot of raw materials of C4 or higher olefins in the world. Considering the influence of various factors including change of chemical product market and transportation cost, it is a preferable way to make use of these raw materials by subjecting them to deep processing on the spot. One hopeful process of which involves the conversion of C4 or higher olefins to lower olefins. The process not only can make use of raw materials of C4 or higher olefins being relatively surplus and having a lower accessory value, but also can obtain various lower olefins products having wide uses.

The reference document CN1490287A disclosed a process for production of ethylene and propylene by reacting a mixture containing $C_4$ or $C_5$ olefins in a fixed-bed reactor at a temperature of 350-500° C., a pressure of 0.6-1.0 MPa and a weight hourly space velocity (WHSV) of 1-10 $hr^{-1}$. It was focused on the modification of various types of catalysts and the reaction results, and the reaction raw materials are mainly directed to $C_4$ and $C_5$ olefins but not to $C_5$ or higher olefins. Meanwhile, a single reactor configuration was used therein, thus it was impossible to assure that the catalyst kept a desirable stability and to obtain a desirable yield of the target products.

The reference document CN1274342A (counterpart to U.S. Pat. No. 6,307,117B1) disclosed a process for producing ethylene and propylene by catalytic conversion from a linear hydrocarbon feedstock containing 20% or more of at least one $C_4$-$C_{12}$ olefins, wherein zeolite in a zeolite-containing catalyst used therein satisfied the following requirements: said zeolite contained substantially no proton, said zeolite had a $SiO_2/Al_2O_3$ molar ratio of from 200 to 5,000, and said zeolite contained at least one metal selected from the group consisting of metals belonging to Group IB of the Periodic Table, and said zeolite was an intermediate pore size zeolite, and the preferred zeolite belonged to the ZSM-5 zeolite family. The reaction was carried at a temperature of 400-700° C., a pressure of 0.1-10 atm and a WHSV of 1-1,000 $hr^{-1}$. However, a single reactor configuration was similarly used therein, thereby resulting in relatively lower yields of ethylene and propylene with the highest yield of propylene being only 25.19%.

The reference document WO 00/26163 to Equistar Chemicals, L.P. disclosed a process for making propylene and ethylene from a feedstock containing at least 60 wt. % $C_4$ and/or $C_5$ olefins with a zeolite catalyst having an intermediate pore size. Zeolites useful in the invention included: zeolites having one-dimensional channel such as ZSM-23 and AlPO4-11 which had a pore diameter greater than 3.5 Å and a pore size index within the range of 14 to 28; and zeolites having interconnecting channels such as ZSM-57 and AlPO4-18 which included a primary channel that had a pore diameter greater than 3.5 Å and a pore size index within the range of 14 to 28, and a secondary channel that had a pore size index less than 20. The catalyst could be Na-type, H-type and etc., in which trace amounts of an oxidizing metal such as Pd or Pt could be added to promote coke removal during catalyst regeneration. The process was used generally with a fixed-bed reactor system, and the reaction was preformed at a temperature of 200-750° C., a pressure of 0.05-1 MPa and a WHSV of 0.5-1,000 $hr^{-1}$. On the one side, the reference did not disclose concrete preparation method of the catalyst and reaction data. Meanwhile, a single reactor configuration was also used therein, which determined the results including non-ideal yields of ethylene and propylene and poor stability of the catalyst.

The reference document EP0109059A1 put forward a process for conversion of $C_4$-$C_{12}$ olefins to propylene. The catalyst used therein was ZSM-5 zeolite having a $SiO_2/Al_2O_3$ molar ratio equal to or lower than 300. The process was carried out at a temperature of 400-600° C., and a space velocity of olefins of higher than 50 $hr^{-1}$. The influences of various formulated raw materials, reaction temperature and space velocity on catalytic cracking reaction were investigated in detail therein. However, it was not mentioned in this invention to use combined reactor configurations, thus the catalyst could not effectuate its advantage of optimum catalytic conversion, and the target product did not have satisfactory selectivity and stability.

The reference document U.S. Pat. No. 5,981,818 put forward a process for conversion of $C_4$-$C_7$ olefins to $C_3$ and $C_4$ olefins. The catalyst used therein was pentasil type zeolite catalyst having a $SiO_2/Al_2O_3$ molar ratio of 10-200, a BET specific surface area of 300-600 $m^2/g$, and a particle size of 0.1-0.9 μm. The reaction temperature was 380-500° C. One feature of this invention resided in blending a certain proportion of vapor into the feedstock, wherein the ratio of $H_2O$/HC was 0.5-3 (by weight). It was said that the addition of vapor could alleviate carbon deposition on the catalyst to thereby increase stability of the catalyst. Likewise, it was not considered in this invention to use combined reactor configuration, which similarly could not effectuate the advantage of optimum activity and stability for the catalyst.

CONTENTS OF THE INVENTION

The technical problem to be solved in the present invention is to overcome the defects presented in the prior documents including poor stability and short life of catalyst, and low yield and selectivity of lower olefins as the target products, and the present invention put forward a novel process for producing lower olefins. After making extensive and intensive analysis on the complicated mechanism of catalytic cracking reaction of olefins, the present inventors have made a lot of experimental researches and explorations, closely combining macroscopic exhibition and microscopic essence of the experimental phenomena, in light of basic principles of heat transfer, thereby put forward a novel technical solution for solving those problems.

The present invention provides a process for producing lower olefins by catalytic cracking a feedstock containing C4 or higher olefins and optionally an organic oxygenate compound. The process is featured with high yield and good selectivity in term of lower olefins as the target product, as well as high stability of the catalyst.

The process for producing lower olefins herein, which is carried out under the conditions of catalytic cracking olefins and adopts as a feedstock an olefins-enriched mixture containing one or more C4 or higher olefins, comprises the steps of:

a) letting the feedstock firstly enter a first reaction zone to contact with a first crystalline aluminosilicate catalyst having a $SiO_2/Al_2O_3$ molar ratio of at least 10, to thereby produce a first reaction effluent containing lower olefins;

b) letting the first reaction effluent enter in turn at least one second reaction zone to contact with a second crystalline aluminosilicate catalyst having a $SiO_2/Al_2O_3$ molar ratio of at least 10, to thereby produce a second reaction effluent containing lower olefins; and c) separating lower olefins from the second reaction effluent;

wherein, the reaction temperature in the first reaction zone is 200-530° C., and the reaction temperature in the second reaction zone is 440-600° C., with the proviso that the first reaction zone has a different reaction temperature from the second reaction zone.

The term "lower olefins" used herein refers to olefins having 2 to 6 carbon atoms.

The olefins-enriched mixture containing one or more C4 or higher olefins used as a feedstock in the above technical solution is preferably an olefins-enriched mixture fraction containing C4 or higher olefins and derived from catalytic cracking units in refinery or from steam cracking units in ethylene factory, or an olefins-enriched mixture component containing C4 or higher olefins and co-produced in the production of alpha-olefins, or by-produced in OTO (from oxygenate to olefin), for example MTO (methanol to olefin), such as MTP (methanol to propylene). The amount of C4 or higher olefins in the olefins-enriched feedstock ranges from 10 to 90% by weight. The olefins-enriched mixture is preferably a mixture containing $C_4$-$C_{12}$ linear olefins, more preferably a mixture containing $C_4$-$C_8$ linear olefins.

The second reaction effluent herein passes in turn such as ethylene separation tower and propylene separation tower to thereby obtain lower olefins product such as ethylene and propylene. Such process of separating lower olefins is well known to a person skilled in the art.

In one preferred embodiment of the invention, an organic oxygenate compound is added at the inlet of at least the first reaction zone, and the weight ratio of the total organic oxygenate compound (including an organic oxygenate compound that may be added at the inlet of the second reaction zone) to olefins in the olefins-enriched mixture is 0.01-10:1. Optionally, an organic oxygenate compound is also added at the inlet of the second reaction zone, and the weight ratio of this portion of organic oxygenate compound to C4 and higher olefins in the olefins-enriched stream at the inlet of the second reaction zone is 0-5:1.

The organic oxygenate compound used herein includes methanol, dimethyl ether, ethanol, ethyl ether or mixtures thereof in any ratio. Preferably, the organic oxygenate compound is methanol, dimethyl ether or a mixture of methanol and dimethyl ether in any ratio. One preferred embodiment of the invention resides in adding a suitable amount of an organic oxygenate compound together with the hydrocarbon feedstock to the reactor. For instance, on the one side, methanol or dimethyl ether as an oxygenate compound is dehydrated under the reaction conditions to form ethylene and propylene which is in favor of increasing the yield of the target products, and meanwhile water as produced may serve as a diluting gas for cracking C4 or higher olefins, and more importantly, methanol or dimethyl ether produces by catalytic cracking at a relatively lower temperature an active intermediate that can activate carbon-carbon bond of hydrocarbons to thereby lower the reaction temperature, and reduce carbon deposition at acidic center of the catalyst. Simultaneously, a certain amount of methanol or dimethyl ether or mixture thereof is supplemented to the effluent from the outlet of each reactor for the purpose of providing heat absorption capacity needed in cracking reaction by the virtue of dehydration-heat liberation of the organic oxygenate compound, and at the same time providing diluting gas, so that the intermediate procedures and energy during the reactions: are effectively utilized by an effective combination of two kinds of the reactions mentioned above.

In one embodiment of the invention, the first reaction zone has a reaction temperature of preferably 200-530° C., more preferably 350-500° C.; a WHSV (the weight of feedstock passed per hour per unit weight of catalyst) of preferably 0.1-100 $hr^{-1}$, more preferably 2-50 $hr^{-1}$; and a reaction pressure (gauge pressure, the same below) of preferably −0.1-5 MPa, more preferably −0.07-0.5 MPa. The second reaction zone has a reaction temperature of preferably 440-600° C., more preferably 470-580° C.; a WHSV of preferably 0.1-100 $hr^{-1}$, more preferably 0.5-30 $hr^{-1}$; and a reaction pressure of preferably −0.1-1 MPa, more preferably −0.07-0.5 MPa.

In another embodiment of the invention, both the first and second reaction zones have a pressure of preferably 0-1 MPa or −0.1-<0 MPa. When adding an organic oxygenate compound at the inlet of at least the first reaction zone, both the first and second reaction zones have a pressure of preferably 0-0.5 MPa or −0.07-<0 MPa.

In another embodiment of the invention, the first reaction zone has a reaction temperature of most preferably 440-480° C., and the second reaction zone has a reaction temperature of most preferably 480-550° C., and the reaction temperature in the first reaction zone is lower than that in the second reaction zone. It is further preferred that the temperature of the first reaction zone is lower by 10-80° C., more preferably 20-50° C., than that of the second reaction zone.

In another embodiment of the invention, the first reaction zone has a WHSV of most preferably 5-30 hr$^{-1}$, and the second reaction zone has a WHSV of most preferably 1-20 hr$^{-1}$, and the WHSV of the first reaction zone is higher than that of the second reaction zone. It is further preferred that the WHSV of the first reaction zone is higher by 5-15 hr$^{-1}$ than that of the second reaction zone.

The first and second crystalline aluminosilicates used herein both are preferably selected from ZSM molecular sieves, beta molecular sieves or mordenite zeolite molecular sieves, having a $SiO_2/Al_2O_3$ molar ratio of at least 10. The ZSM molecular sieves are more preferably selected from ZSM-5, ZSM-11, ZSM-23 or ZSM-42, having a $SiO_2/Al_2O_3$ molar ratio of preferably 10-3,000. Both of the first and second crystalline aluminosilicates are, most preferably, ZSM-5 molecular sieves having a $SiO_2/Al_2O_3$ molar ratio of 50-500.

In the process of the invention, said at least one of the second reaction zones preferably includes 1-5 reactors in series, more preferably 1-3 fixed-bed reactors in series. In which, the fixed-bed reactor is preferably selected from axial fixed-bed or radial fixed-bed reactors.

In one preferred embodiment, the invention adopts at least two reaction zones in series, wherein, in comparison, the first reaction zone is operated at a higher WHSV and a lower temperature, and the second reaction zone is operated at a lower WHSV and a higher temperature. A lot of experimental researches demonstrate that the mechanism of catalytic cracking process of C4 or higher olefins is polymerization-and-cracking mechanism, wherein the polymerization process is exothermic, and the cracking process is endothermic. The centralized liberation of heat during the polymerization may cause a relatively greater temperature increase of the catalyst at the inlet, in particular the local temperature at active center of the catalyst may be higher by tens or even above 100 centigrade than the apparent temperature of the catalyst, and a too high local temperature increase has a very fatal influence on the life of the catalyst. In particular, it may greatly promote the processes of the aromatization of olefins on the catalyst and olefin condensation to produce coke, thereby accelerating coking and thus deactivation of the catalyst and shortening its stable period. As for the catalytic cracking process of olefins, a too high local temperature increase has an even more notable influence on the life of the catalyst.

A lower temperature operation used in the first reaction zone may alleviate thermal discharge from polymerization of olefins, to thereby avoid, during the polymerization of olefins, a too high local temperature increase that may cause rapid deactivation of the catalyst. Meanwhile, a relatively higher WHSV is used therein for the purpose of avoiding overmuch hydrogen transfer reactions at lower temperature that may reduce the yield and selectivity of the target products. In addition, considering that the cracking process of olefins is endothermic, a relatively higher operation temperature and a relatively lower WHSV are used in the second reaction zones connected in series, so as to guarantee sufficient heat absorption and retention time for the cracking process of olefins, to thereby fulfill the purpose of maximizing the yield of lower olefins and prolonging the stable period of the catalyst. It is very important for increasing yield of lower olefins by using fixed-bed catalytic cracking process.

The technical solution of the invention achieves a preferable technical effect, which effectively prolongs the stability of the catalyst activity with the proviso of lowering the reaction temperature and increasing the yield and selectivity of lower olefins as the target products.

Reference could be made to conventional catalytic cracking process of lower olefins with respect to other operation conditions that are not specifically described herein but may be involved in the present process for producing lower olefins by catalytic cracking.

Unless identified otherwise, the percentages and ratios used herein are all on the basis of weight.

Unless identified otherwise, the $SiO_2/Al_2O_3$ molar ratio of the crystalline aluminosilicates in the present invention is calculated on atomic basis.

All the publications mentioned are incorporated herein for reference in their entirety for all purposes. The following examples further describe and demonstrate the preferred embodiments of the present inventions. AR of the examples are merely illustrative, not interpreted as limiting to the present inventions.

In the examples, the amounts of various components in each of the mixtures involved are separated and detected with HP-6890 gas chromatograph (Agilent Technologies, Inc., the United States), equipped with a hydrogen flame ion detector and a $\Phi$0.53 mm PLOT $Al_2O_3$ capillary chromatographic column of length of 50 meters.

EXAMPLES

Example 1

Raw materials in a molar ratio of $200SiO_2$: 0.5 $Al_2O_3$: 60 n-butyl amine: 17 OH$^-$: 200 NaCl: 6300 $H_2O$ were mixed with stirring at room temperature for 15 hr to formulate a slurry containing silicon, aluminum, template (n-butyl amine) and water in light of a $SiO_2/Al_2O_3$ molar ratio of 200. Thereafter, the slurry was crystallized at 140° C. for 50 hr, followed by washing the crystallized solution with distilled water, drying it at 120° C. in an air atmosphere for 12 hr and then calcining it at 580° C. in an air atmosphere for 8 hr to obtain ZSM-5 molecular sieve. 50 g of the ZSM-5 molecular weight was mixed with 87 g of 40% (weight) silica gel, and extruded to obtain strips followed by drying them at 130° C. in an air atmosphere for 12 hr and calcining at 430° C. in an air atmosphere for 6 hr to obtain a ZSM-5 type catalyst.

5 g of the above ZSM-5 type catalyst was respectively loaded into first and second reactors in series (both of which are $\Phi$18 mm axial fixed-bed reactors, the same in the following examples, unless identified otherwise), and activated at 480° C. in a $N_2$ atmosphere for 3 hr prior to reaction. Then, a $C_4$ feedstock was charged to react by contacting with the catalyst. The first reactor had a reaction temperature of 400° C. and a WHSV of 50 hr$^{-1}$, and the second reactor had a reaction temperature of 530° C. and a WHSV of 12 hr$^{-1}$, and the reaction pressure in both of the two reactors was normal pressure. The $C_4$ feedstock used in the experiment was obtained from FCC apparatus in Shanghai Petrochemical Refinery of SINOPEC (Shanghai city, China), the weight percent amounts of components in the feedstock was shown in Table 1, and the product was analyzed by sampling after reacting for 2 hr (the same in the following examples). The reaction results were listed in Table 2.

TABLE 1

The weight percent amounts of components in the above mixed $C_4$ feedstock obtained from the above FCC apparatus

| Components | Amount, weight % | Components | amount weight % |
|---|---|---|---|
| Isobutane | 3.249 | 1-butene | 51.857 |
| n-Butane | 13.368 | Isobutene | 0.048 |
| Propadiene | 0.068 | Cis-2-butene | 13.211 |
| Acetylene | 0.008 | Isopentane | 0.002 |
| Neopentane | 0.149 | n-Pentane | 0.000 |
| Trans-2-butene | 17.259 | 1,3-butadiene | 0.110 |
| Pentene and isohexane | 0.127 | Methylacetylene | 0.004 |
| n-Hexane | 0.007 | $C_6$ or higher | 0.531 |

TABLE 2

The weight percent composition of the product

| Components | Amount weight % | Components | amount weight % |
|---|---|---|---|
| Hydrogen | 0.073 | Isobutene | 8.963 |
| Methane | 0.208 | Cis-2-butene | 4.060 |
| Ethane | 0.276 | Pentane | 0.777 |
| Ethylene | 6.72 | Isopentane | 2.645 |
| Propane | 4.153 | n-pentane | 1.166 |
| Cyclopropane | 0.003 | Pentene and isohexane | 11.111 |
| Propene | 24.36 | N-hexane | 2.154 |
| Isobutane | 9.358 | Neopentane | 0.159 |
| n-butane | 17.380 | Trans-2-butene | 4.938 |
|  |  | 1-butene | 4.655 |

Wherein, the conversion of C4 was 72.5%, the yield of ethylene was 6.72%, the yield of propylene was 24.36%, and the total yield of ethylene and propylene was 31.08%.

Examples 2-5

The various steps and conditions were the same in these examples as those in Example 1, except that: the ZSM-5 molecular sieve catalyst had a $SiO_2/Al_2O_3$ molar ratio of 500; the first reactor had a reaction temperature of 450° C., a WHSV of 18 $hr^{-1}$ and a reaction pressure of 0.2 MPa; and the second reactor had a reaction temperature of 560° C., a reaction pressure of −0.02 MPa, and a WHSV that varies as described in Table 3. The feedstock used therein was mixed $C_8$ mono-olefin (which was from Lanzhou Refinery of PetroChina Company Limited (Lanzhou city, China), wherein the weight percent of octene was about 80.5%, and the weight percent of octane was about 19.5%). The reaction results were listed in Table 3.

TABLE 3

The reaction results with a feedstock of mixed $C_8$ mono-olefin

| | Example No. | | | |
|---|---|---|---|---|
| | Example 2 | Example 3 | Example 4 | Example 5 |
| WHSV ($hr^{-1}$) | 10.5 | 20.3 | 30.6 | 40.4 |
| Conversion of C8 olefin % | 75.92 | 74.09 | 72.63 | 70.06 |
| Selectivity of ethylene % | 10.00 | 10.56 | 11.04 | 12.51 |
| Selectivity of propylene % | 28.06 | 30.64 | 33.32 | 36.69 |
| Selectivity of (E + P) % | 38.49 | 42.30 | 46.12 | 52.99 |
| Yield of ethylene % | 7.59 | 7.83 | 8.01 | 8.76 |
| Yield of propylene % | 21.30 | 22.70 | 24.20 | 25.70 |
| Yield of (E + P) % | 28.89 | 30.53 | 32.21 | 34.46 |

Notes:
E referred to ethylene;
P referred to propylene; and
E + P referred to the sum of ethylene and propylene Examples 6-11

The various steps and conditions in these examples were same in this example as those in Example 1, except that: the first reactor was loaded with a ZSM-5 molecular sieve catalyst having a $SiO_2/Al_2O_3$ molar ratio of 60, and the second reactor was loaded with a ZSM-5 molecular sieve catalyst having a $SiO_2/Al_2O_3$ molar ratio of 480; both of the catalysts were activated at 480° C. in a $N_2$ atmosphere for 3 hr prior to reaction.

The $C_4$ feedstock used in the reaction was obtained from FCC in the above refinery, whose components were shown in Table 1. The first and second reactors respectively adopted different reaction schemes as in Table 4. The reaction results were listed in Table 4.

TABLE 4

The reaction results of different reaction schemes

| | Reaction conditions | Reaction temperature | WHSV ($hr^{-1}$) | Pressure MPa | Yield of ethylene | Yield of propylene |
|---|---|---|---|---|---|---|
| Example 6 | Conditions in the first reactor | 210 | 50 | 4.5 | 4.63 | 20.90 |
| | Conditions in the second reactor | 440 | 10 | 0.015 | | |
| Example 7 | Conditions in the first reactor | 400 | 20 | −0.04 | 6.21 | 25.26 |
| | Conditions in the second reactor | 500 | 20 | −0.072 | | |
| Example 8 | Conditions in the first reactor | 530 | 2 | −0.06 | 5.20 | 20.11 |

TABLE 4-continued

The reaction results of different reaction schemes

| Reaction conditions | | Reaction temperature | WHSV (hr$^{-1}$) | Pressure MPa | Yield of ethylene | Yield of propylene |
|---|---|---|---|---|---|---|
| | Conditions in the second reactor | 560 | 35 | 0.02 | | |
| Example 9 | Conditions in the first reactor | 350 | 45 | 2 | 5.90 | 23.90 |
| | Conditions in the second reactor | 510 | 10 | −0.05 | | |
| Example 10 | Conditions in the first reactor | 500 | 90 | 1 | 8.23 | 31.86 |
| | Conditions in the second reactor | 580 | 0.5 | −0.08 | | |
| Example 11 | Conditions in the first reactor | 450 | 5 | −0.06 | 6.50 | 24.36 |
| | Conditions in the second reactor | 470 | 1 | −0.01 | | |

Example 12

The various steps and conditions in this example were the same as those in Example 1, except that: the molecular sieve was ZSM-5 molecular sieve catalyst having a SiO$_2$/Al$_2$O$_3$ molar ratio of 300; the first reactor had a reaction temperature of 410° C., a WHSV of 70 hr$^{-1}$ and a reaction pressure of −0.053 MPa; and the second reactor had a reaction temperature of 500° C., a WHSV of 1.5 hr$^{-1}$ and a reaction pressure of 0 MPa. The feedstock used herein was the mixed C$_4$ feedstock obtained from the above FCC apparatus, whose components by weight percent were shown in Table 1. The reaction results were as follows: the yield of ethylene was 4.37%, the yield of propylene was 22.51%, and the conversion of C$_4$ olefins was 70.5%.

Example 13

The various steps and conditions in this example were the same as those in Example 1, except that: the molecular sieve was ZSM-11 molecular sieve catalyst having a SiO$_2$/Al$_2$O$_3$ molar ratio of 300; the first reactor had a reaction temperature of 470° C., a WHSV of 5 hr$^{-1}$ and a reaction pressure at normal pressure; and the second reactor had a reaction temperature of 560° C., a WHSV of 1.5 hr$^{-1}$ and a reaction pressure of 0 MPa. The feedstock used herein was the mixed C$_4$ feedstock obtained from the above FCC apparatus, whose components by weight percent were shown in Table 1. The reaction results were as follows: the yield of ethylene was 5.10%, the yield of propylene was 20.03%, and the conversion of C$_4$ olefins was 68.23%.

Example 14

The various steps and conditions in this example were the same as those in Example 1, except that: the molecular sieve was ZSM-23 molecular sieve catalyst having a SiO$_2$/Al$_2$O$_3$ molar ratio of 350; the first reactor had a reaction temperature of 470° C., a WHSV of 5 hr$^{-1}$ and a reaction pressure of 0 MPa; and the second reactor had a reaction temperature of 560° C., a WHSV of 1.5 hr$^{-1}$ and a reaction pressure of 0 MPa. The feedstock used herein was the mixed C$_4$ olefins obtained from the FCC apparatus of the above refinery, whose components by weight percent were shown in Table 1. The reaction results were as follows: the yield of ethylene was 6.07%, the yield of propylene was 21.68%, and the conversion of C$_4$ olefins was 71.8%.

Example 15

The various steps and conditions were the same in this example as those in Example 1, except that: the molecular sieve was ZSM42 molecular sieve catalyst having a SiO$_2$/Al$_2$O$_3$ molar ratio of 210; the first reactor had a reaction temperature of 470° C., a WVSV of 5 hr$^{-1}$ and a reaction pressure of 0 MPa; and the second reactor had a reaction temperature of 560° C., a WHSV of 1.5 hr$^{-1}$ and a reaction pressure of 0 MPa. The feedstock used herein was mixed C$_4$ olefins obtained from the above FCC apparatus, whose components by weight percent were shown in Table 1. The reaction results were as follows: the yield of ethylene was 6.92%, the yield of propylene was 19.37%, and the conversion of C$_4$ olefins was 73.8%.

Example 16

The various steps and conditions were the same in this example as those in Example 1, except that: the molecular sieve was beta molecular sieve catalyst having a SiO$_2$/Al$_2$O$_3$ molar ratio of 700; the first reactor had a reaction temperature of 470° C., a WHSV of 5 hr$^{-1}$ and a reaction pressure of 0 MPa; and the second reactor had a reaction temperature of 560° C., a WHSV of 1.5 hr$^{-1}$ and a reaction pressure of 0 MPa. The feedstock used herein was the mixed C$_4$ olefins obtained from the above FCC apparatus, whose components by weight percent were shown in Table 1. The reaction results were as follows: the yield of ethylene was 6.46%, the yield of propylene was 21.15%, and the conversion of C$_4$ olefins was 72.3%.

Example 17

The various steps and conditions were the same in this example as those in Example 1, except that: the molecular sieve was mordenite molecular sieve catalyst having a SiO$_2$/Al$_2$O$_3$ molar ratio of 30; the first reactor had a reaction temperature of 530° C., a WHSV of 28 hr$^{-1}$ and a reaction pressure of 0 MPa; and the second reactor had a reaction temperature of 580° C., a WHSV of 5 hr$^{-1}$ and a reaction pressure at normal pressure. The feedstock used herein was mixed Q feedstock (wherein the weight amount of n-pentene was 44.1%, that of n-pentane was 15.28%, and that of iso-pentane was 40.62%) obtained from steam cracking unit in Ethylene Factory of SINOPEC SHANGHAI Petrochemical Company limited (Shanghai city, China). The reaction results were as follows: the yield of ethylene was 8.75%, the yield of propylene was 26.19%, the yield of butylene is 30.5%, and the conversion of C$_5$ olefins was 76.1%.

Example 18

The various steps and conditions were the same in this example as those in Example 1, except that: the feedstock for catalytic cracking was C$_4$-C$_7$ mono-olefins obtained from by-products in the production of olefins by cracking methanol in Shanghai Research Institute of Petrochemical Technology SINOPEC (Shanghai city, China), wherein the amounts of C$_4$ and C$_5$ olefins were respectively about 60% and about 25%, with the remaining about 15% being C$_6$ or higher olefins. The first reactor had a reaction temperature of 530° C., a WHSV of 28 hr$^{-1}$ and a reaction pressure of 0 MPa; and the second reactor had a reaction temperature of 580° C., a WHSV of 5 hr$^{-1}$ and a reaction pressure of 0.2 MPa. The molecular sieve in both the first and second reactors was ZSM-5 molecular sieve catalyst having a SiO$_2$/Al$_2$O$_3$ molar ratio of 480. The catalyst was activated at 480° C. in a N$_2$ atmosphere for 3 h prior to the reaction. The reaction results were as follows: the yield of ethylene was 6.31%, the yield of propylene was 21.53%, and the conversion of total olefins was 69.1%.

Example 19

The various steps and conditions were the same in this example as those in Example 12, except that: the reactor included a first rector, a second reactor and a third reactor connected in series; the catalyst used in any of the reactors was ZSM-5 molecular sieve catalyst having a SiO$_2$/Al$_2$O$_3$ molar ratio of 300; the first reactor had a reaction temperature of 410° C., a WHSV of 70 hr$^{-1}$ and a reaction pressure of –0.053 MPa; the second reactor had a reaction temperature of 450° C., a WHSV of 50 hr$^{-1}$ and a reaction pressure of 0 MPa; and the third reactor had a reaction temperature of 480° C., a WHSV of 2 hr$^{-1}$ and a reaction pressure of 0 MPa. The feedstock used herein was mixed C$_4$ olefins obtained from the above FCC apparatus in the refinery, whose components by weight percent were shown in Table 1. The reaction results were as follows: the yield of ethylene was 5.12%, the yield of propylene was 22.87%, and the conversion of C$_4$ olefins was 71.2%.

Example 20

The various steps and conditions were the same in this example as those in Example 19, except that: a fourth reactor was connected in series behind the third reactor; the catalyst used in any of the reactors was ZSM-5 molecular sieve catalyst having a SiO$_2$/Al$_2$O$_3$ molar ratio of 300; the first reactor had a reaction temperature of 410° C., a WHSV of 70 hr$^{-1}$ and a reaction pressure of –0.053 MPa; the second reactor had a reaction temperature of 450° C., a WHSV of 50 hr$^{-1}$ and a reaction pressure of 0 MPa; the third reactor had a reaction temperature of 480° C., a WHSV of 48 hr$^{-1}$ and a reaction pressure of 0 MPa; and the fourth reactor had a reaction temperature of 500° C., a WHSV of 2 hr$^{-1}$ and a reaction pressure of 0 MPa. The feedstock used herein was mixed C$_4$ olefins obtained from the above FCC apparatus in the refinery, whose components by weight percent were shown in Table 1. The reaction results were as follows: the yield of ethylene was 5.72%, the yield of propylene was 23.31%, and the conversion of C4 olefins was 71.5%.

Example 21

The various steps and conditions were the same in this example as those in Example 20, except that: a fifth reactor was connected in series behind the fourth reactor; the catalyst used in any of the reactors was ZSM-5 molecular sieve catalyst having a SiO$_2$/Al$_2$O$_3$ molar ratio of 300; the first reactor had a reaction temperature of 410° C., a WHSV of 70 hr$^{-1}$ and a reaction pressure of –0.053 MPa; the second reactor had a reaction temperature of 450° C., a WHSV of 50 hr$^{-1}$ and a reaction pressure of 0 MPa; the third reactor had a reaction temperature of 480° C., a WHSV of 48 hr$^{-1}$ and a reaction pressure of 0 MPa; the fourth reactor had a reaction temperature of 500° C., a WHSV of 30 hr$^{-1}$ and a reaction pressure of 0 MPa; and the fifth reactor had a reaction temperature of 530° C., a WHSV of 2 hr$^{-1}$ and a reaction pressure of 0 MPa. The feedstock used herein was mixed C$_4$ feedstock obtained from the above FCC apparatus in the refinery, whose components by weight percent were shown in Table 1. The reaction results were as follows: the yield of ethylene was 6.41%, the yield of propylene was 23.96%, and the conversion of C$_4$ olefins was 72.0%.

Example 22

The various steps and conditions were the same in this example as those in Example 21, except that: a sixth reactor was connected in series behind the fifth reactor; the catalyst used in any of the reactors was ZSM-5 molecular sieve catalyst having a SiO$_2$/Al$_2$O$_3$ molar ratio of 300; the first reactor had a reaction temperature of 410° C., a WHSV of 70 hr$^{-1}$ and a reaction pressure of –0.053 MPa; the second reactor had a reaction temperature of 450° C., a WHSV of 50 hr$^{-1}$ and a reaction pressure of 0 MPa; the third reactor had a reaction temperature of 480° C., a WHSV of 48 hr$^{-1}$ and a reaction pressure of 0 MPa; the fourth reactor had a reaction temperature of 500° C., a WHSV of 30 hr$^{-1}$ and a reaction pressure of 0 MPa; the fifth reactor had a reaction temperature of 530° C., a WHSV of 28 hr$^{-1}$ and a reaction pressure of 0 MPa; and the sixth reactor had a reaction temperature of 550° C., a WHSV of 2 hr$^{-1}$ and a reaction pressure of 0 MPa. The feedstock used herein was mixed C$_4$ feedstock obtained from the above FCC apparatus in the refinery, whose components by weight percent were shown in Table 1. The reaction results were as follows: the yield of ethylene was 6.83%, the yield of propylene was 24.06%, and the conversion of C$_4$ olefins was 72.8%.

Example 23

The various steps and conditions were the same in this example as those in Example 1, except that: the first reactor had a reaction temperature of 470° C. and a WHSV of 12.0 hr$^{-1}$; the second reactor had a reaction temperature of 550° C. and a WHSV of 12 hr$^{-1}$; the reaction pressure in both of the reactors was normal pressure. The feedstock being mixed C$_4$ feedstock (whose components by weight percent were shown in Table 1) obtained from the above FCC apparatus in the refinery was used for investigating the life of the catalyst. The reaction results were listed in Table 5.

TABLE 5

Reaction results of combined reactors

| Reaction time (hr) | Conversion of C4 olefins % | Yield of propylene % | Yield of ethylene % |
|---|---|---|---|
| 1.00 | 71.37 | 21.41 | 6.61 |
| 7.00 | 71.69 | 22.65 | 6.85 |
| 13.00 | 68.67 | 21.62 | 6.33 |
| 19.00 | 68.75 | 21.77 | 6.15 |
| 25.00 | 68.00 | 21.99 | 6.13 |
| 31.00 | 70.03 | 22.79 | 6.32 |
| 37.00 | 73.42 | 21.28 | 6.08 |
| 43.00 | 73.56 | 21.35 | 6.00 |
| 49.00 | 67.93 | 24.05 | 6.39 |
| 55.00 | 62.29 | 22.30 | 5.79 |
| 61.00 | 69.71 | 20.72 | 5.14 |
| 67.00 | 69.86 | 20.46 | 5.02 |
| 73.00 | 66.98 | 22.69 | 5.47 |
| 79.00 | 64.94 | 23.97 | 5.86 |
| 85.00 | 62.43 | 22.65 | 5.41 |
| 91.00 | 64.44 | 22.92 | 5.36 |
| 97.00 | 65.65 | 23.42 | 5.32 |
| 103.00 | 66.28 | 23.67 | 5.30 |
| 115.00 | 62.84 | 22.09 | 4.77 |
| 121.00 | 65.36 | 22.51 | 4.77 |
| 127.00 | 65.54 | 23.49 | 4.96 |
| 133.00 | 61.67 | 22.60 | 4.65 |
| 139.00 | 62.21 | 21.99 | 4.51 |
| 145.00 | 61.90 | 21.71 | 4.35 |
| 173.00 | 61.88 | 22.41 | 3.82 |
| 179.00 | 61.15 | 22.33 | 3.73 |
| 187.00 | 62.53 | 23.42 | 3.83 |
| 195.00 | 60.38 | 22.02 | 3.44 |
| 203.00 | 60.32 | 22.15 | 3.36 |
| 211.00 | 61.42 | 23.21 | 3.38 |
| 219.00 | 59.12 | 21.59 | 3.06 |
| 227.00 | 58.62 | 22.57 | 3.07 |
| 235.00 | 57.98 | 22.64 | 3.03 |
| 243.00 | 57.99 | 20.74 | 2.67 |
| 251.00 | 57.03 | 22.07 | 2.75 |

Comparative Example 1

The life of the same ZSM-5 molecular sieve catalyst was investigated according to the various steps and conditions as described in Example 23 except that: a single reactor was used with a reaction temperature of 550° C., a reaction pressure at normal pressure, and a WHSV being identical with the total WHSV as given in Example 23. The results were listed in Table 6.

TABLE 6

Investigation on life of the catalyst with a single reactor

| Reaction time (hr) | Conversion of C4 olefins % | Yield of propylene % | Yield of ethylene, % |
|---|---|---|---|
| 0.50 | 71.17 | 24.52 | 8.73 |
| 3.50 | 70.59 | 26.51 | 9.32 |
| 6.50 | 68.97 | 25.38 | 8.31 |
| 10.50 | 70.81 | 24.91 | 8.70 |
| 14.50 | 70.51 | 25.43 | 8.74 |
| 23.00 | 70.44 | 26.13 | 8.93 |
| 32.00 | 70.18 | 25.01 | 8.53 |
| 36.00 | 65.71 | 24.51 | 7.91 |
| 40.00 | 68.82 | 25.09 | 8.26 |
| 44.00 | 68.56 | 24.79 | 7.98 |
| 48.00 | 67.42 | 25.27 | 8.08 |
| 52.00 | 68.88 | 24.54 | 7.72 |
| 56.00 | 67.36 | 25.36 | 7.68 |
| 60.00 | 67.97 | 25.09 | 7.59 |
| 64.00 | 67.72 | 25.01 | 7.47 |
| 70.00 | 66.75 | 25.88 | 7.72 |

TABLE 6-continued

Investigation on life of the catalyst with a single reactor

| Reaction time (hr) | Conversion of C4 olefins % | Yield of propylene % | Yield of ethylene, % |
|---|---|---|---|
| 76.00 | 65.29 | 24.89 | 6.89 |
| 80.00 | 61.68 | 23.96 | 5.93 |
| 84.00 | 64.70 | 24.58 | 6.70 |
| 88.00 | 63.79 | 24.19 | 6.30 |
| 92.00 | 62.99 | 25.21 | 6.68 |
| 98.00 | 62.74 | 23.69 | 6.01 |
| 102.00 | 61.49 | 23.81 | 5.85 |
| 106.00 | 60.49 | 23.27 | 5.57 |
| 110.00 | 59.24 | 22.87 | 5.22 |
| 114.00 | 58.12 | 23.02 | 5.26 |
| 120.00 | 57.00 | 22.76 | 5.10 |
| 124.00 | 54.82 | 21.87 | 4.63 |
| 128.00 | 53.32 | 20.85 | 4.34 |
| 132.00 | 51.91 | 19.64 | 3.89 |
| 136.00 | 49.49 | 19.80 | 3.82 |
| 142.00 | 47.39 | 18.67 | 3.41 |
| 146.00 | 43.40 | 17.43 | 2.89 |
| 150.00 | 43.44 | 18.04 | 3.11 |
| 154.00 | 41.83 | 16.62 | 2.69 |
| 158.00 | 40.10 | 15.79 | 2.49 |
| 164.00 | 35.71 | 14.60 | 2.19 |
| 168.00 | 31.45 | 12.81 | 1.79 |
| 172.00 | 31.71 | 12.48 | 1.82 |
| 176.00 | 30.93 | 11.39 | 1.62 |
| 180.00 | 27.44 | 10.53 | 1.43 |
| 186.00 | 28.22 | 10.14 | 1.38 |
| 190.00 | 23.78 | 8.16 | 0.97 |
| 194.00 | 20.98 | 7.80 | 0.93 |
| 198.00 | 22.46 | 8.46 | 1.07 |
| 204.00 | 16.80 | 6.57 | 0.76 |
| 212.00 | 15.39 | 5.88 | 0.76 |
| 218.00 | 12.45 | 5.11 | 0.55 |

Obviously, the technical solution of the present invention could markedly prolong the active period of the catalyst, which had obvious technical advantage.

Comparative Example 2

The various steps and conditions were the same as those described in Example 17 except that: a single reactor was used with a reaction temperature of 580° C., a reaction pressure at normal pressure, and a WHSV being identical with the total WHSV as given in Example 17. The results were as follows: the yield of ethylene was 8.63%, the yield of propylene is 25.21%, and the yield of butylene is 27.6%.

Example 1A

Two reactors in series were used in the reaction. The catalyst was ZSM-5 catalyst as prepared in the above Example 1. The first reactor had a reaction temperature of 400° C., a WHSV of 50 hr$^{-1}$, and a weight ratio of methanol/olefins in the feedstock of 1.5:1; and the second reactor had a reaction temperature of 530° C., a WHSV of 12 hr$^{-1}$, and a weight ratio of methanol to C$_4$ and higher olefins in the feedstock at the outlet of the first reactor of 0.7:1; and the reaction pressure in both of the reactors was normal pressure. The feedstock used in the reaction was mixed C$_4$ feedstock (whose components by weight percent were shown in Table 1) obtained from the above FCC apparatus in the refinery. The reaction results were as follows: the yield of ethylene was 8.96%, the yield of propylene was 28.32%, and the conversion of $C_4$ olefins was 69%.

Examples 2A-7A

The distributions of catalytic cracking products were investigated under the conditions of loading different catalysts in the first and second reactors and using feedstocks having different formulating ratios.

The various steps and conditions were the same in this example as those in Example 1A, except that: the catalyst had a different $SiO_2/Al_2O_3$ molar ratio; and the catalyst was activated at 480° C. in a $N_2$ atmosphere for 3 h prior to the reaction. In which, the mixed $C_4$ feedstock was obtained from the above FCC apparatus in the refinery, whose components by weight percent were shown in Table 1; and the mixed $C_5$ feedstock was identical with that used in Example 17; and mixed $C_8$ mono-olefin feedstock was identical with that used in Examples 2-5.

The reaction conditions in the first and second reactors and the relevant reaction results were shown in Table 2A.

were as follows: the yield of ethylene was 9.10%, the yield of propylene was 31.03%, and the conversion of $C_4$ olefins was 69.57%.

Examples 9A

The various steps and conditions were the same in this example as those in Example 1A, except that: the catalyst was ZSM-23 molecular sieve catalyst having a $SiO_2A_2O_3$ molar ratio of 350; the first reactor had a reaction temperature of 470° C., a WHSV of 5 $hr^{-1}$, a reaction pressure of 0 MPa, and a weight ratio of methanol/olefins in the feedstock of 0.1:1; and the second reactor had a reaction temperature of 560° C., a WHSV of 1.5 $hr^{-1}$, a reaction pressure of 0 MPa, and a weight ratio of methanol to $C_4$ and higher olefins in the stream at the inlet of the second reactor of 0.8:1. The feedstock used in the reaction was mixed $C_4$ olefins (whose components by weight percent were shown in Table 1) obtained from the above FCC apparatus in the refinery. The reaction results were as follows: the yield of ethylene was 7.09%, the yield of propylene was 28.13%, and the conversion of $C_4$ olefins was 70.5%.

TABLE 2A

|  |  | Example No. | | | | | |
| --- | --- | --- | --- | --- | --- | --- | --- |
|  |  | 2A | 3A | 4A | 5A | 6A | 7A |
|  | Feedstock | Mixed $C_8$ mono-olefin | Mixed $C_4$ (FCC) | Pure 1-butene | Mixed $C_5$ | Pure 1-butene | Pure 1-butene |
| The first reactor | Temperature(?) | 300 | 400 | 450 | 350 | 480 | 480 |
|  | Pressure (MPa) | 0.5 | −0.04 | −0.06 | 0.3 | 0 | −0.05 |
|  | WHSV ($hr^{-1}$) | 50 | 20 | 10 | 45 | 30 | 25 |
|  | methanol? olefins in the feedstock | 0.1 | 1 | 0.8 | 0.5 | 1.5 | 0.5 |
|  | Catalyst ($SiO_2/Al_2O_3$ molar ratio) | 200 | 100 | 100 | 50 | 80 | 120 |
| The second reactor | Temperature (?) | 520 | 500 | 560 | 510 | 580 | 570 |
|  | Pressure (MPa) | 0.045 | −0.072 | 0.02 | −0.05 | 0 | −0.05 |
|  | WHSV ($hr^{-1}$) | 10 | 15 | 35 | 10 | 5 | 8 |
|  | methanol? C4 and higher olefins in the stream at the inlet of the second reactor | 0 | 0.2 | 2.5 | 1 | 3 | 0 |
|  | catalyst ($SiO_2/Al_2O_3$ molar ratio) | 200 | 500 | 300 | 200 | 280 | 120 |
| Reaction results | Yield of ethylene | 8.63 | 7.12 | 9.8 | 10.0 | 12.2 | 11.0 |
|  | Yield of propylene | 26.9 | 29.72 | 32.64 | 33.16 | 36.2 | 35.8 |
|  | olefins Conversion | 74.81 | 73.12 | 70.67 | 71.18 | 74.9 | 73.59 |

Example 8A

The various steps and conditions were the same in this example as those in Example 1A, except that: the catalyst was ZSM-11 molecular sieve catalyst having a $SiO_2/A_2O_3$ molar ratio of 310; the first reactor had a reaction temperature of 460° C., a WHSV of 5 $hr^{-1}$, a reaction pressure of 0 MPa, and a weight ratio of methanol/olefins in the feedstock of 0.05:1; and the second reactor had a reaction temperature of 565° C., a WHSV of 1.5 $hr^{-1}$, a reaction pressure of 0 MPa, and a weight ratio of methanol to $C_4$ and higher olefins in the stream at the inlet of the second reactor of 0.2:1. The feedstock used in the reaction was mixed $C_4$ olefins (whose components by weight percent were shown in Table 1) obtained from the above FCC apparatus in the refinery. The reaction results

Example 10A

The various steps and conditions were the same in this example as those in Example 1A, except that: the catalyst was ZSM42 molecular sieve catalyst having a $SiO_2/Al_2O_3$ molar ratio of 210; the first reactor had a reaction temperature of 470° C., a WHSV of 5 $hr^{-1}$, a reaction pressure of 0 MPa, and a weight ratio of methanol/olefins in the feedstock of 5:1; and the second reactor had a reaction temperature of 560° C., a WHSV of 1.5 $hr^{-1}$, a reaction pressure of 0 MPa, and a weight ratio of methanol to $C_4$ and higher olefins in the stream at the inlet of the second reactor of 3:1. The feedstock used in the reaction was mixed $C_4$ olefins (whose components by weight percent were shown in Table 1) obtained from the above FCC apparatus in the refinery. The reaction results were as follows:

the yield of ethylene was 11.54%, the yield of propylene was 37.66%, and the conversion of $C_4$ olefins was 75.87%.

Example 11A

The various steps and conditions were the same in this example as those in Example 1A, except that: the catalyst was beta molecular sieve catalyst having a $SiO_2/Al_2O_3$ molar ratio of 700; the first reactor had a reaction temperature of 470° C., a WHSV of 5 $hr^{-1}$, a reaction pressure of 0 MPa, and a weight ratio of methanol/olefins in the feedstock of 0.5:1; and the second reactor had a reaction temperature of 560° C., a WHSV of 1.5 $hr^{-1}$, a reaction pressure of 0 MPa, and a weight ratio of methanol to $C_4$ and higher olefins in the stream at the inlet of the second reactor of 0.3:1. The feedstock used in the reaction was mixed $C_4$ olefins (whose components by weight percent were shown in Table 1) obtained from the above FCC apparatus in the refinery. The reaction results were as follows: the yield of ethylene was 8.43%, the yield of propylene was 29.19%, and the conversion of $C_4$ olefins was 72.8%.

Example 12A

The various steps and conditions were the same in this example as those in Example 1A, except that: the catalyst was mordenite molecular sieve catalyst having a $SiO_2/Al_2O_3$ molar ratio of 30; the first reactor had a reaction temperature of 530° C., a WHSV of 28 $hr^{-1}$, a reaction pressure of 0 MPa, and a weight ratio of methanol/olefins in the feedstock of 8.5:1; and the second reactor had a reaction temperature of 580° C., a WHSV of 5 $hr^{-1}$, a reaction pressure of 0 MPa, and a weight ratio of methanol to $C_4$ and higher olefins in the stream at the inlet of the second reactor of 0.08:1. The feedstock used in the reaction was mixed C5 feedstock. The reaction results were as follows: the yield of ethylene was 10.69%, the yield of propylene was 33.84%, and the conversion of $C_5$ olefins was 72.3%.

Example 13A

The various steps and conditions were the same in this example as those in Example 1A, except that: the feedstock was $C_4$-$C_7$ mono-olefins as used in Example 18.
The first reactor had a reaction temperature of 530° C., a WHSV of 28 $hr^{-1}$, a reaction pressure of 0 MPa, and a weight ratio of methanol/olefins in the feedstock of 0.05:1; and the second reactor had a reaction temperature of 580° C., a WHSV of 5 $hr^{-1}$, a reaction pressure of 0.2 MPa, and a weight ratio of methanol to $C_4$ and higher olefins in the stream at the inlet of the second reactor of 0.08:1. The catalyst used in both the first and second reactors was ZSM-5 molecular sieve catalyst having a $SiO_2/Al_2O_3$ molar ratio of 480. The catalyst was activated at 480° C. in a $N_2$ atmosphere for 3 hr prior to reaction. The reaction results were as follows: the yield of ethylene was 11.31%, the yield of propylene was 32.73%, and the conversion of total olefins was 73.7%.

Example 14A

The various steps and conditions were the same in this example as those in Example 13A, except that: three fixed-bed reactors in series were used in the reaction. The catalyst used in any of these reactors was ZSM-5 molecular sieve catalyst having a $SiO_2/Al_2O_3$ molar ratio of 300. The first reactor had a reaction temperature of 410° C., a WHSV of 70 $hr^{-1}$, a reaction pressure of –0.053 MPa, and a weight ratio of methanol/olefins in the feedstock of 0.05:1; the second reactor had a reaction temperature of 450° C., a WHSV of 50 $hr^{-1}$, a reaction pressure of 0 MPa, and a weight ratio of methanol to $C_4$ and higher olefins in the stream at the inlet of the second reactor of 0; and the third reactor had a reaction temperature of 480° C., a WHSV of 2 $hr^{-1}$, a reaction pressure of 0 MPa, and a weight ratio of methanol to $C_4$ and higher olefins in the stream at the inlet of the third reactor of 0.08:1. The feedstock used in the reaction was mixed $C_4$ olefins (whose components by weight percent were shown in Table 1) obtained from the above FCC apparatus in the refinery. The reaction results were as follows: the yield of ethylene was 11.82%, the yield of propylene was 36.87%, and the conversion of $C_4$ olefins was 72.2%.

Example 15A

The various steps and conditions were the same in this example as those in Example 14A, except that: four fixed-bed reactors in series were used in the reaction. The catalyst used in any of these reactors was ZSM-5 molecular sieve catalyst having a $SiO_2/Al_2O_3$ molar ratio of 300. The first reactor had a reaction temperature of 410° C., a WHSV of 70 $hr^{-1}$, a reaction pressure of –0.053 MPa, and a weight ratio of methanol/olefins in the feedstock of 0.05:1; the second reactor had a reaction temperature of 480° C., a WHSV of 50 $hr^{-1}$, a reaction pressure of 0 MPa, and a weight ratio of methanol to $C_4$ and higher olefins in the stream at the inlet of the second reactor of 0.05:1; the third reactor had a reaction temperature of 460° C., a WHSV of 48 $hr^{-1}$, a reaction pressure of 0 MPa, and a weight ratio of methanol to $C_4$ and higher olefins in the stream at the inlet of the third reactor of 0.08:1; and the fourth reactor had a reaction temperature of 530° C., a WHSV of 2 $hr^{-1}$, a reaction pressure of 0 MPa, and a weight ratio of methanol to $C_4$ and higher olefins in the stream at the inlet of the fourth reactor of 0.08:1. The feedstock used in the reaction was mixed $C_4$ olefins (whose components by weight percent were shown in Table 1) obtained from the above FCC apparatus in the refinery. The reaction results were as follows: the yield of ethylene was 11.90%, the yield of propylene was 34.01%, and the conversion of $C_4$ olefins was 75.5%.

Example 16A

The various steps and conditions were the same in this example as those in Example 15A, except that: five fixed-bed reactors in series were used in the reaction. The catalyst used in any of these reactors was ZSM-5 molecular sieve catalyst having a $SiO_2/Al_2O_3$ molar ratio of 300. The first reactor had a reaction temperature of 410° C., a WHSV of 70 $hr^{-1}$, a reaction pressure of –0.053 MPa, and a weight ratio of methanol/olefins in the feedstock of 0.05:1; the second reactor had a reaction temperature of 480° C., a WHSV of 50 $hr^{-1}$, a reaction pressure of 0 MPa, and a weight ratio of methanol to $C_4$ and higher olefins in the stream at the inlet of the second reactor of 0.05:1; the third reactor had a reaction temperature of 500° C., a WHSV of 48 $hr^{-1}$, a reaction pressure of 0 MPa, and a weight ratio of methanol to $C_4$ and higher olefins in the stream at the inlet of the third reactor of 0.08:1; the fourth reactor had a reaction temperature of 480° C., a WHSV of 30 $hr^{-1}$, a reaction pressure of 0 MPa, and a weight ratio of methanol to $C_4$ and higher olefins in the stream at the inlet of the fourth reactor of 0.08:1; and the fifth reactor had a reaction temperature of 530° C., a WHSV of 2 $hr^{-1}$, a reaction pressure of 0 MPa, and a weight ratio of methanol to $C_4$ and higher olefins in the stream at the inlet of the fifth reactor of 0.08:1. The feedstock used in the reaction was mixed $C_4$ olefins (whose components by weight percent were shown in Table 1) obtained from the above FCC apparatus in the refinery. The reaction results were as follows: the yield of ethylene was 1241%, the yield of propylene was 33.36%, and the conversion of $C_4$ olefins was 76.8%.

Example 17A

The catalyst used in the reaction was ZSM-5 type molecular sieve catalyst made according to the various steps described in Example 1. The catalyst was activated at 480° C. in a $N_2$ atmosphere for 3 hr prior to reaction.

Two axial fixed-bed reactors in serials are used in the reaction, wherein the first reactor had a reaction temperature of 470° C., a WHSV of 12 $hr^{-1}$, and a weight ratio of methanol/olefins in the feedstock of 0.01:1; and the second reactor had a reaction temperature of 550° C., a WHSV of 12 $hr^{-1}$, and a weight ratio of methanol/$C_4$ and higher olefins in the stream at the inlet of the second reactor of 0.01:1; and the reaction pressure in both of the reactors was normal pressure. The feedstock being mixed $C_4$ olefins (whose components by weight percent were shown in Table 1) obtained from the above FCC apparatus was used for investigating the life of the catalyst. The reaction results were listed in Table 3A.

TABLE 3A

| Reaction (hr) | Conversion of $C_4$ olefins | Yield of ethylene % | Yield of propylene, % |
|---|---|---|---|
| 0 | 71.03 | 9.56 | 29.65 |
| 6 | 72.27 | 9.98 | 31.04 |
| 12 | 71.40 | 9.75 | 31.33 |
| 30 | 69.65 | 9.00 | 30.22 |
| 60 | 67.79 | 8.83 | 30.70 |
| 66 | 70.16 | 9.40 | 31.84 |
| 84 | 69.54 | 9.36 | 32.57 |
| 108 | 69.15 | 9.03 | 32.00 |
| 150 | 67.18 | 8.70 | 31.81 |
| 186 | 67.15 | 8.42 | 31.55 |
| 240 | 66.24 | 7.87 | 31.22 |
| 270 | 66.07 | 7.73 | 31.17 |
| 300 | 67.12 | 7.73 | 31.19 |
| 324 | 65.47 | 7.51 | 31.70 |
| 330 | 66.51 | 7.69 | 31.55 |
| 354 | 66.99 | 7.33 | 30.54 |

Comparison Example 1A

The life of the same ZSM-5 molecular sieve catalyst was investigated according to the various steps and conditions as described in Example 17A except that: a single reactor was used, which had a reaction temperature of 550° C., a reaction pressure at normal pressure, and a WHSV being identical with the total WHSV as given in Example 17A, without adding methanol. The results were listed in Table 4A.

TABLE 4A

| Reaction time (hr) | Conversion of $C_4$ olefins | Yield of propylene | Yield of ethylene |
|---|---|---|---|
| 0.50 | 71.17 | 24.52 | 8.73 |
| 10.50 | 70.81 | 24.91 | 8.70 |
| 23.00 | 70.44 | 26.13 | 8.93 |
| 36.00 | 65.71 | 24.51 | 7.91 |
| 44.00 | 68.56 | 24.79 | 7.98 |
| 52.00 | 68.88 | 24.54 | 7.72 |
| 64.00 | 67.72 | 25.01 | 7.47 |
| 88.00 | 63.79 | 24.19 | 6.30 |
| 102.00 | 61.49 | 23.81 | 5.85 |
| 114.00 | 58.12 | 23.02 | 5.26 |
| 150.00 | 43.44 | 18.04 | 3.11 |
| 180.00 | 27.44 | 10.53 | 1.43 |
| 194.00 | 20.98 | 7.80 | 0.93 |
| 212.00 | 15.39 | 5.88 | 0.76 |
| 218.00 | 12.45 | 5.11 | 0.55 |

Obviously, the present technical solution of adding methanol could similarly markedly prolong the active period of the catalyst, which had obvious technical advantage.

The invention claimed is:

1. A process for producing lower olefins, which is carried out under the conditions of catalytic cracking olefins and adopts as a feedstock an olefins-enriched mixture containing one or more C4 or higher olefins, comprises the steps of:
   a) introducing the feedstock firstly enter a first reaction zone to contact with a first crystalline aluminosilicate catalyst having a $SiO_2/Al_2O_3$ molar ratio of at least 10, to thereby produce a first reaction effluent containing lower olefins;
   b) introducing the first reaction effluent enter in turn at least one second reaction zone to contact with a second crystalline aluminosilicate catalyst having a $SiO_2/Al_2O_3$ molar ratio of at least 10, to thereby produce a second reaction effluent containing lower olefins; and
   c) separating lower olefins from the second reaction effluent;
   wherein the reaction temperature in the first reaction zone is lower by 10 to 80° C. than that in the second reaction zone and the WHSV of the first reaction zone is higher by 5-15 $hr^{-1}$ than that of the second reaction zone.

2. The process as claimed in claim 1, wherein the olefins-enriched mixture is an olefins-enriched mixture fraction containing C4 or higher olefins and derived from catalytic cracking units in refinery or from steam cracking units in ethylene factory, or an olefins-enriched mixture component containing C4 or higher olefins and co-produced in the production of alpha-olefins, or by-produced in oxygenate to olefin.

3. The process as claimed in claim 1, wherein the olefins-enriched mixture is a mixture containing $C_4$-$C_{12}$ linear olefins.

4. The process as claimed in claim 3, wherein the olefins-enriched mixture is a mixture containing $C_4$-$C_8$ linear olefins.

5. The process as claimed in claim 1, wherein an organic oxygenate compound is added at the inlet of at least the first reaction zone, and the weight ratio of the total organic oxygenate compound to olefins in the olefins-enriched mixture is 0.01-10:1.

6. The process as claimed in claim 1, wherein an organic oxygenate compound is added at the inlet of the second reaction zone, and the weight ratio of this portion of the organic oxygenate compound to $C_4$ and higher olefins in the olefins-enriched stream at the inlet of the second reaction zone is 0-5:1.

7. The process as claimed in claim 5, wherein the organic oxygenate compound is methanol, dimethyl ether, or mixture of methanol and dimethyl ether.

8. The process as claimed in claim 1, wherein the first reaction zone has a WHSV of 0.1-100 $hr^{-1}$, a reaction pressure of −0.1-5 MPa; and the second reaction zone has a WHSV of 0.1-100 $hr^{-1}$, a reaction pressure of −0.1-1 MPa.

9. The process as claimed in claim 8, wherein the first reaction zone has a reaction temperature of 350-500° C., a WHSV of 2-50 hr$^{-1}$, and a reaction pressure of –0.07-0.5 MPa; and the second reaction zone has a reaction temperature of 470-580° C., a WHSV of 0.5-30 hr$^{-1}$, and a reaction pressure of –0.07-0.5 MPa.

10. The process as claimed in claim 8, wherein the reaction pressure in both the first and second reaction zones is 0-1 MPa.

11. The process as claimed in claim 8, wherein, when adding an organic oxygenate compound at the inlet of at least the first reactor, the reaction pressure in both the first and second reaction zones is 0-0.5 MPa.

12. The process as claimed in claim 9, wherein the first reaction zone has a reaction temperature of 440-480° C., and the second reaction zone has a reaction temperature of 480-550° C.

13. The process as claimed in claim 9, wherein the first reaction zone has a WHSV of 5-30 hr$^{-1}$, and the second reaction zone has a WHSV of 1-20 hr$^{-1}$.

14. The process as claimed in claim 1, wherein the first and second crystalline aluminosilicates both are selected from ZSM molecular sieves, beta molecular sieves or mordenite molecular sieves.

15. The process as claimed in claim 14, wherein the ZSM molecular sieve is selected from ZSM-5, ZSM-11, ZSM-23 or ZSM-42; and the molecular sieve has a $SiO_2/Al_2O_3$ molar ratio of 10-3,000.

16. The process as claimed in claim 11, wherein the first and second crystalline aluminosilicates both are selected from ZSM-5 molecular sieves having a $SiO_2/Al_2O_3$ molar ratio of 50-500.

17. The process as claimed in claim 1, wherein at least one of the second reaction zones includes 1-5 reactors in series.

18. The process as claimed in claim 17, wherein at least one of the second reaction zones includes 1-3 fixed-bed reactors in series.

19. The process as claimed in claim 1, wherein the reactors used in both the first reaction zone and the second reaction zone are selected from axial fixed-bed reactors, and radial fixed-bed reactors.

20. The process as claimed in claim 8, wherein the reaction pressure in both the first and second reaction zones is –0.1 to less than 0 MPa.

21. The process as claimed in claim 8, wherein, when adding an organic oxygenate compound at the inlet of at least the first reactor, the reaction pressure in both the first and second reaction zones is –0.07 to less than 0 MPa.

22. The process as claimed in claim 1, wherein the reaction temperature in the first reaction zone is 200-530° C. and the reaction temperature in the second reaction zone is 440-600° C.

* * * * *